United States Patent [19]

Fiege et al.

[11] Patent Number: 5,591,869
[45] Date of Patent: Jan. 7, 1997

[54] PROCESS FOR THE PREPARATION OF METHYLENE COMPOUNDS AND THE NOVEL COMPOUND 2-(2,4-DICHLORO-5-FLUOROBENZYL)THIOPHENE

[75] Inventors: Helmut Fiege; Ferdinand Hagedorn, both of Leverkusen, Germany

[73] Assignee: Bayer Aktiengesellschaft, Leverkusen, Germany

[21] Appl. No.: 568,050

[22] Filed: Dec. 6, 1995

[30] Foreign Application Priority Data

Dec. 16, 1994 [DE] Germany ............... 44 44 862.7

[51] Int. Cl.$^6$ .................... C07D 333/12; C07D 307/38
[52] U.S. Cl. ............... 549/80; 549/504; 549/505; 549/77; 549/496
[58] Field of Search ............... 549/80, 29, 504, 549/505, 77, 496

[56] References Cited

U.S. PATENT DOCUMENTS

| | | | |
|---|---|---|---|
| 3,579,538 | 5/1971 | Meyer et al. | 549/77 |
| 5,288,751 | 2/1994 | Brooks et al. | 549/77 |
| 5,426,196 | 6/1995 | Fang | 549/307 |

FOREIGN PATENT DOCUMENTS 9411342  5/1994  WIPO.

OTHER PUBLICATIONS

Houben–Weyl, "Methoden de der organischen Chemie", vo. 11d, p. 267 (1981).
C. Lau et al, J. Org. Chem., vol. 54, pp. 491–494 (1989).
A. Ono et al, Synthesis, pp. 736–765 (1987).
G. Gribble et al, Synthesis, pp. 763–765 (1978).
J. March, "Advanced Organic Chemistry", 2nd Ed., pp. 1119–1121, McGraw–Hill, New York (1977).
B. R. Brown, et al., Journal of the Chemical Society, pp. 3755–3757, (1957).
R. F. Nystrom, et al., Journal of the American Chemical Society, vol. 80, No. 11, pp. 2896–2898, (1958).
J. March, Advanced Organic Chemistry, pp. 490–493, (1984).

Primary Examiner—José G. Dees
Assistant Examiner—Deborah Lambkin
Attorney, Agent, or Firm—Sprung Horn Kramer & Woods

[57] ABSTRACT

Methylene compounds are preferably prepared by reducing an aluminum halide complex of the formula

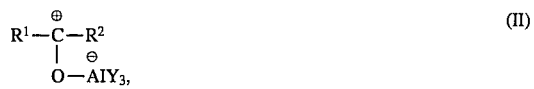

in which $R^1$ represents a $C_6$–$C_{10}$-aryl radical which is optionally substituted by 1 to 4 $C_1$–$C_4$-alkyl radicals, 1 to 4 fluorine, chlorine and/or bromine atoms, one $C_1$–$C_8$-alkoxy group and/or one acetoxy group, or represents a heteroaryl radical which is optionally substituted by one $C_1$–$C_4$-alkyl radical and/or one fluorine, chlorine or bromine atom and contains 5 to 10 C atoms and one O or S atom and $R^2$ represents a $C_1$–$C_{12}$-alkyl radical which is optionally substituted by 1 to 5 fluorine, chlorine and/or bromine atoms, independently of $R^1$ represents a radical as defined for $R^1$ and, in the case where $R^1$=a $C_6$–$C_{10}$-aryl radical which is substituted by 1 to 4 fluorine, chlorine and/or bromine atoms, also represents a furyl or thienyl radical, Y represents fluorine, chlorine or bromine, with an amineborane of the formula

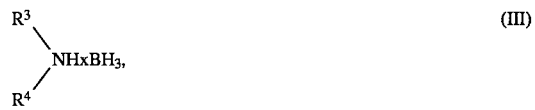

in which $R^3$ represents $C_1$–$C_4$-alkyl and $R^4$ represents hydrogen or $C_1$–$C_4$-alkyl and/or with sodium borohydride and/or with potassium borohydride.

2-(2,4-Dichloro-5-fluorobenzyl)thiophene is obtainable in this way for the first time.

11 Claims, No Drawings

PROCESS FOR THE PREPARATION OF METHYLENE COMPOUNDS AND THE NOVEL COMPOUND 2-(2,4-DICHLORO-5-FLUOROBENZYL)THIOPHENE

The present invention relates to a particularly advantageous process for the preparation of methylene compounds. Methylene compounds are important intermediates for the preparation of a wide variety of active compounds. The present invention also relates to 2-(2,4-dichloro-5-fluorobenzyl)thiophene which has become available for the first time using this process. For example, 2-(4-fluorobenzyl)thiophene and 2-(4-fluorobenzyl)furan represent important building blocks for the preparation of active compounds which are leukotriene biosynthesis inhibitors (see U.S. Pat. No. 5,288,751).

It is known that methylene compounds can be prepared by reduction of ketones by the Wolff-Kishner and Huang Minion methods (see J. March, Advanced Organic Chemistry, McGraw-Hill, pages 1119–1121 (1977)). These methods require the handling of hydrazine, which one seeks to avoid for ecological reasons. In addition, reduction processes of these types fail with ketones whose hydrazones can be prepared only with difficulty and in those cases in which substituents on the ketones can also react with hydrazine.

Furthermore the reduction of ketones with sodium borohydride and tert-butylamine-borane in the presence of anhydrous aluminum chloride is known (see Synthesis, pages 736–738 (1987) and J. Org. Chem. 54, 491–494 (1989)). The amounts of aluminum chloride and, in particular, of sodium borohydride or tert-butylamine-borane required in these processes are extremely high at 3 to 5 mol/mol of ketone, so that this process is disadvantageous because of the required amounts of auxiliaries.

The reduction of ketones with sodium borohydride in trifluoroacetic acid as reaction medium has also been described (see Synthesis, pages 763–765 (1978)). In this case, the industrial handling of trifluoroacetic acid is problematic because of its corrosivity, its solubility in water and the azeotrope formation with water, and its high price.

2-(4-Fluorobenzyl)thiophene has been prepared by another synthetic route by the action of 2-thienyllithium on 4-fluorobenzyl bromide in the presence of tetrakis-(triphenylphosphine)-palladium(0) at −78° C. in diethyl ether/tetrahydrofuran. Although the yield is good at 81%, the preparation method is extremely elaborate and not very suitable for industrial use (see U.S. Pat. No. 5,288,751, Example 12A).

Ketones can be prepared by acylation of acid halides or anhydrides with aromatic or heteroaromatic compounds using aluminium trihalides by the Friedel-Crafts method. During the course of this reaction the elimination of hydrogen chloride in many cases results in an aluminium halide complex which is soluble in the particular reaction medium used. This aluminium halide complex is then normally hydrolysed by introduction into ice-water to obtain the ketone. Ketone obtained in this way can be reduced with boron-hydrogen compounds alone only to the carbinol stage but not to the methylene stage (see Houben-Weyl, Methoden der organischen Chemie [Methods of Organic Chemistry], Volume 4/1d, page 267 (1981)).

A process for the preparation of methylene compounds of the formula $$R^1\text{—}CH_2\text{—}R^2 \quad (I)$$

in which

R$^1$ represents a C$_6$–C$_{10}$-aryl radical which is optionally substituted by 1 to 4 C$_1$–C$_4$-alkyl radicals; 1 to 4 fluorine, chlorine and/or bromine atoms, one C$_1$–C$_8$-alkoxy group and/or one acetoxy group, or represents a heteroaryl radical which is optionally substituted by one C$_1$–C$_4$-alkyl radical and/or one fluorine, chlorine or bromine atom and contains 5 to 10 C atoms and one O or S atom and R$^2$ represents a C$_1$–C$_{12}$-alkyl radical which is optionally substituted by 1 to 5 fluorine, chlorine and/or bromine atoms, independently of R$^1$ represents a radical as defined for R$^1$ and, in the case where R$^1$=a C$_6$–C$_{10}$-aryl radical which is substituted by 1 to 4 fluorine, chlorine and/or bromine atoms, also represents a furyl or thienyl radical, has now been found, which is characterized in that an aluminium halide complex of the formula

      (II)

in which

R$^1$ and R$^2$ have the abovementioned meaning, and

Y represents fluorine, chlorine or bromine, is reduced with an amineborane of the formula

      (III)

in which

R$^3$ represents C$_1$–C$_4$-alkyl and

R$^4$ represents hydrogen or C$_1$–C$_4$-alkyl and/or with sodium borohydride and/or with potassium borohydride.

Aluminium halide complexes of the formula (II) can be obtained in principle by two routes, namely a) by Friedel-Crafts acylation of an aromatic or heteroaromatic compound of the formula $$R^1\text{—}H \quad (IV)$$

in which

R$^1$ has the abovementioned meaning, with acyl compounds of the formula $$R^2\text{—}COX \quad (V)$$

in which

R$^2$ has the abovementioned meaning, and

X represents fluorine, chlorine or bromine, or b) by Friedel-Crafts acylation of a compound of the formula $$R^2\text{—}H \quad (VI)$$

in which

R$^2$ has the abovementioned meaning, with an acyl compound of the formula $$R^1\text{—}COX \quad (VII)$$

in which

R$^1$ and X have the abovementioned meanings.

Success is not achieved with both routes in all cases, but always is with at least one. If R$^2$ represents an alkyl or aryl radical, route a) is preferred, and if R$^2$ represents a furyl or thienyl radical, route b) is.

This procedure for the preparation of the aluminium halide complex of the formula (II) and its reduction according to the invention provides the advantage of avoiding additional reaction steps hitherto necessary, for example the working up, isolation, purification and drying of the particular ketone; the renewed use of aluminium halide in the reduction; multistage procedure; handling of large amounts of auxiliaries; handling of corrosive and costly chemicals. Isolation of the aluminium halide complex of the formula (II) is unnecessary. It can be further processed in the form of the reaction mixture resulting from its preparation.

The process according to the invention is single-stage, starts from readily accessible starting compounds, requires only relatively small amounts of auxiliaries and requires no corrosive and/or costly chemicals.

$R^1$ in the formulae (I), (II), (IV) and (VII) preferably represents a phenyl radical which is unsubstituted or substituted by 1 to 4 fluorine, chlorine and/or bromine atoms, or represents a heteroaryl radical containing 5 C atoms and one S or O atom.

$R^2$ in the formulae (I), (II), (V) and (VI) preferably represents a phenyl radical which optionally contains 1 to 3 substituents from the group consisting of fluorine and chlorine, or, if $R^1$ represents a $C_6$–$C_{10}$-aryl radical which is substituted by 1 to 4 fluorine, chlorine and/or bromine atoms, also represents a furyl or thienyl radical.

X in the formulae (V) and (VII) preferably represents chlorine or bromine and, independently thereof, Y in formula (III) likewise represents chlorine or bromine.

$R^3$ in formula (III) preferably represents methyl, ethyl or tert-butyl and $R^4$ preferably represents hydrogen, methyl or ethyl.

Particularly preferred starting materials of the formulae (IV) and (VI) are thiophene, benzothiophene, benzofuran, fluorobenzene and 2,4-dichlorofluorobenzene.

Particularly preferred starting materials of the formulae (V) and (VII) are 4-fluorobenzoyl chloride, 4-chlorobenzoyl chloride, 2,4-dichloro-5-fluorobenzoyl chloride, 2-chloro-4,5-difluorobenzoyl chloride, thenoyl chloride and furoyl chloride.

Particularly preferred amineboranes of the formula (III) are dimethylamineborane and tert-butylamineborane. The use of sodium borohydride and potassium borohydride is likewise preferred.

The following methylene compounds of the formula (I) are particularly preferably prepared by the process according to the invention: 2-(4-fluorobenzyl)thiophene, 2-(4-chlorobenzyl)thiophene, 2-(4-fluorobenzyl)furan, 2-(2,4-dichloro-5-fluorobenzyl)-thiophene, 2-(2-chloro-4,5-difluorobenzyl)thiophene and 2-(2,4-dichloro-5-fluorobenzyl)furan.

The process according to the invention can be carried out by the following method, for example:

An acyl compound of the formula (V) or (VII) is reacted with a compound of the formula (IV) or (VI) with addition of an aluminium halide in an inert diluent with elimination of hydrogen halide. After removal of the hydrogen halide, for example by applying a vacuum, the resulting reaction mixture which contains an aluminium halide complex of the formula (II) is reacted with an amineborane of the formula (III) or sodium borohydride or potassium borohydride, the mixture is hydrolysed with water to eliminate the aluminium halide, the aqueous phase is separated off, and the organic phase is distilled.

Suitable inert diluents are solvents which are customary in Friedel-Craft acylations and which must additionally be inert to boron-hydrogen compounds. Halogenobenzenes and ethers, especially chlorobenzene, o-dichlorobenzene and mixtures of chlorobenzene and diglyme, are preferred.

The procedure up to the stage of the reaction mixtures containing the aluminium halide complex of the formula (II) can be like that known for the preparation of ketones from aromatic compounds and acyl compounds by the Friedel-Crafts method (see, for example, Houben-Weyl, Methoden der organischen Chemie [Methods of Organic Chemistry], Volume VII/2a, pages 15 et seq. (1973)).

The reduction according to the invention of aluminium halide complexes of the formula (II) with one of the stated boron-hydrogen compounds can be carded out, for example, at 0° to 100° C., preferably at 50° to 90° C. It is advantageous to use an additional solvent in this reduction, for example an ether, especially when the boron-hydrogen compound has low solubility in the reaction medium which is otherwise present. Preferred additional solvents are tetrahydrofuran, diethylene glycol dimethyl ether (diglyme) and ethylene glycol dimethyl ether.

A solution or suspension which contains the boron-hydrogen compound in for example, digylme is preferably added to the solution or suspension which contains the aluminium halide complex of the formula (II).

It is perfectly possible for the reaction temperature in the acylation and reduction reaction steps to be different. Thus, for example, the reaction of an acyl compound of the formula (V) or (VII) with a compound of the formula (IV) or (VI) can be started initially in the low temperature range, for example at −10° to +10° C., and be raised during the course of the reaction to 50° to 110° C. By contrast, the reduction can be carried out in the temperature range from 0° to 100° C., preferably 50° to 90° C.

The amount of boron-hydrogen compound to be used per mole of aluminium halide complex of the formula (II) can be, for example, 0.5 to 1 mol, preferably 0.7 to 0.8 mol. A larger excess of reducing agent does not in general improve the result but entails the risk of perhydrogenation of aromatic or heterocyclic radicals.

It is possible for the first time with the process according to the invention to prepare 2-(2,4-dichloro-5-fluorobenzyl)thiophene of the formula

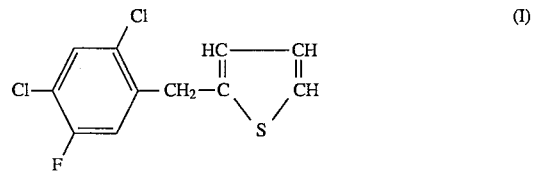

(I)

(see Example 4). The present invention therefore also relates to the compound of the formula (I). Lipoxygenase inhibitors and inhibitors for leukotriene biosynthesis can be prepared from the compound of the formula (I), as is known for other 2-benzylthiophenes (see WO 90/12008 and U.S. Pat. No. 5,288,751).

EXAMPLES

Example 1

2-(4-Fluorobenzyl)thiophene 33.8 g of aluminium trichloride were suspended in 217 g of chlorobenzene, and a solution of 40.3 g of 4-fluorobenzoyl chloride in 37.4 g of chlorobenzene was added dropwise to this at 0° C. over the course of 15 minutes. The mixture was then stirred for 1 hour and then, at 0° C., 21.8 g of thiophene were added dropwise over the course of 20 minutes. The resulting hydrogen chloride was drawn off and absorbed in sodium hydroxide solution. The mixture was subsequently heated to 80° C. and the remaining hydrogen chloride was removed. The resulting solution was added dropwise to a suspension of 7.2 g of sodium borohydride in 47.2 g of digylme while stirring at 70° C. over the course of 45 minutes. The reaction mixture was then stirred for 90 minutes and then cooled to room temperature and discharged into a mixture of 250 g of ice, 44.6 g of concentrated aqueous hydrochloric acid and 500 g of water. The organic phase which formed thereby was separated off, the aqueous phase was extracted by shaking with chlorobenzene, and the combined organic phases were distilled. 35.0 g of product with a boiling point of 83° C./1.0 mbar and a purity of 99.7% (GC) were obtained. This corresponds to 73.9% of theory. The product contained less than 0.1% by weight of defluorinated compounds (GC).

Example 2

2-Benzylthiophene 27.2 g of 98.5% pure aluminium trichloride (sublimed) were suspended in 130 ml of chlorobenzene and cooled to 0° C. 28.7 g of benzoyl chloride were added dropwise while stirring and cooling over the course of 30 minutes, and the mixture was then stirred for 1 hour. Likewise at 0° C., a solution of 17.3 g of thiophene in 27 ml of chlorobenzene was added dropwise over the course of 30 minutes, and the mixture was stirred for 1 hour. Remaining hydrogen chloride was driven out by heating the mixture and stirring, finally under vacuum. The remaining solution was introduced over the course of 40 minutes into a solution of 12.7 g of dimethylamineborane in 70 ml of chlorobenzene while stirring at 70° C. The mixture was then stirred for 1 hour, cooled and discharged into a mixture of 200 g of ice and 50 g of concentrated aqueous hydrochloric acid while stirring. The aqueous phase was then separated off and extracted with chlorobenzene. The remaining organic phase was extracted by shaking with water. The organic phase and the extract from the aqueous phase were then combined, the solvent was removed therefrom by distillation, and 38.7 g of crude 2-benzylthiophene of 79.7% purity were obtained by distillation. This corresponds to 88.5% of theory. Redistillation resulted in 99.7% pure 2-benzylthiophene with a boiling point of 91° to 92° C./1.4 mbar.

EXAMPLE 3

2-(4-Fluorobenzyl)thiophene 33.8 g of aluminium chloride were suspended in 200 g of fluorobenzene, and a solution of 37.8 g of thiophene-2-carbonyl chloride in 50 ml of fluorobenzene was added dropwise to this at 0° C. over the course of 30 minutes. The mixture was stirred at 0° C. for 2 hours and then slowly warmed, and heated under reflux at 85° C. for 2 hours until evolution of hydrogen chloride ceased. The solution was cooled to 70° C. and then, at this temperature, added dropwise over the course of 30 minutes to a stirred suspension of 7.2 g of of sodium borohydride in 50 ml of diglyme. The mixture was then stirred at 70° C. for 90 minutes and, after cooling, discharged into a mixture of 250 g of ice, 200 ml of water and 62.5 g of concentrated aqueous hydrochloric acid. After addition of 100 ml of fluorobenzene, the organic phase was separated off, extracted by shaking with 100 ml of water and concentrated. Yield: 58.3 g of product with a content of 61.8% by weight of 2-(4-fluorobenzyl)thiophene (GC), corresponding to a yield of 75.1% of theory. An organic phase was obtained from the aqueous mother liquor by extraction with methylene chloride and concentration and contained a further 33.7% by weight of the required product (GC), corresponding to an additional yield of 4.6% of theory. Distillation of the organic phase resulted in a 99.2% pure 2-(4-fluorobenzyl)thiophene.

Example 4

2-(2,4-Dichloro-5-fluorobenzyl)thiophene 3.8 g of aluminium chloride were suspended in 162.5 ml of chlorobenzene, and a solution of 58.9 g of 2,4-dichloro-5-fluorobenzoyl chloride in 33.8 ml of chlorobenzene was added dropwise to this at 0° C. over the course of 30 minutes. The mixture was stirred at 0° C. for 90 minutes and then, at 0° C., a solution of 21.8 g of thiophene in 33.8 ml of chlorobenzene was added dropwise over the course of 30 minutes. The mixture was stirred at 0° C. for a further 2 hours and finally heated to reflux for 15 minutes until evolution of hydrogen chloride ceased. The resulting solution was added dropwise to a suspension of 7.2 g of sodium borohydride in 50 ml of diglyme at 70° C. over the course of 30 minutes, and the reaction mixture was subsequently stirred at 70° C. for 90 minutes and then discharged into a mixture of 250 g of ice, 200 ml of water and 62.5 g of concentrated aqueous hydrochloric acid. After addition of 100 ml of chlorobenzene and stirring, the phases were separated. The organic phase was extracted by shaking with 100 ml of water and was subsequently concentrated. Yield: 78.5 g of crude substance with a content of 76.7% by weight (GC) of 2-(2,4-dichloro-5-fluorobenzyl)thiophene, corresponding to 92.3% of theory. Distillation resulted in a 97.2% pure (GC) product, boiling point 140° to 145° C./8 mbar, melting point 60° to 61° C.

Example 5

2-(4-Methylbenzyl)thiophene 39 g of 4-methylbenzoyl chloride were added dropwise to a suspension of 33.8 g of aluminium chloride in 162.5 ml of chlorobenzene while stirring at 0° C. over the course of 30 minutes. The mixture was stirred at 0° C. for 90 minutes and subsequently, at 0° C., a solution of 21.8 g of thiophene in 33.8 ml of chlorobenzene was added dropwise over the course of 30 minutes. The mixture was stirred at 0° C. for 2 hours and then heated under reflux for 15 minutes until evolution of hydrogen chloride ceased. The resulting solution was added dropwise over the course of 30 minutes to a suspension of 7.2 g of sodium borohydride in 50 ml of diglyme heated to 70° C. The mixture was stirred at 70° C. for 1.5 hours and then discharged into a mixture of 250 g of ice, 200 ml of water and 62.5 g of concentrated aqueous hydrochloric acid. After addition of 100 ml of chlorobenzene and thorough stirring, the organic phase was separated off, washed with 100 ml of water and concentrated by distillation. Yield: 57.7 g of crude substance, 71.0% pure (GC), corresponding to a yield of 87.2% of theory. Distillation resulted in a 99.4% pure 2-(4-methylbenzyl)thiophene with boiling point 98° C./4 mbar.

Example 6

2-(4-Chlorobenzyl)thiophene 44.2 g of 4-chlorobenzoyl chloride were introduced over the course of 15 minutes into a suspension of 33.8 g of aluminium chloride and 162.5 ml of chlorobenzene stirred at 0° C., and the mixture was stirred for 90 minutes. Then, at 0° C., a solution of 21.8 g of thiophene in 33.8 ml of chlorobenzene was added dropwise while stirring over the course of 30 minutes. The mixture was stirred at 0° C. for 2 hours and then heated to reflux for 15 minutes until evolution of hydrogen chloride ceased.

The resulting solution was subsequently added dropwise over the course of 30 minutes to a suspension of 7.2 g of sodium borohydride and 50 ml of diglyme heated to 70° C. The mixture was stirred at 70° C. for 90 minutes and then discharged into a mixture of 250 g of ice, 200 ml of water and 62.5 g of concentrated hydrochloric acid. After addition of 100 ml of chlorobenzene, the organic phase was separated off and concentrated. Yield: 66.2 g of crude substance, 73.4% pure (GC). Distillation resulted in a 99.4% pure (GC) 2-(4-chlorobenzyl)thiophene, boiling point 122° C./3.5 mbar.

Example 7

2-(4-Fluorobenzyl)furan

A solution of 34.4 g of furan-2-carbonyl chloride (95% pure) in 50 g of fluorobenzene was added dropwise to a suspension of 33.8 g of aluminium chloride in 200 g of fluorobenzene at room temperature while stirring over the course of 30 minutes. The mixture was heated to 60° C. and then stirred for 1 hour and subsequently at 80° C. for a further 90 minutes. The mixture obtained in this way was added dropwise to a solution of 22.8 g of dimethylaminoborane and 60 g of fluorobenzene while stirring at 60° C. over the course of 85 minutes. The mixture was stirred at 70° C. for 80 minutes and subsequently discharged into a mixture of 250 g of ice, 200 ml of water and 66 g of concentrated hydrochloric acid.

After vigorous stirring of the mixture, separation and washing of the organic phase with water and extraction of the aqueous phase with methylene chloride, the combined organic phases were concentrated. Yield: 50.4 g of 67% pure product (GC), corresponding to 77% of theory. Distillation resulted in a 96% pure 2-(4-fluorobenzyl)furan, boiling point 70° C./3 mbar.

What is claimed is:

1. A process for the preparation of a methylene compound of the formula

 (I)

in which
$R^1$ represents a $C_6$–$C_{10}$-aryl radical which is unsubstituted or substituted by 1 to 4 $C_1$–$C_4$-alkyl radicals, 1 to 4 fluorine, chlorine and/or bromine atoms, one $C_1$–$C_8$-alkoxy group and/or one acetoxy group, or represents a heteroaryl radical which is unsubstituted or substituted by one $C_1$–$C_4$-alkyl radical and/or one fluorine, chlorine or bromine atom and contains 5 to 10 C atoms and one O or S atom and
$R^2$ represents a $C_1$–$C_{12}$-alkyl radical which is unsubstituted or substituted by 1 to 5 fluorine, chlorine and/or bromine atoms, independently of $R^1$ represents a radical as defined for $R^1$ and, in the case where $R^1$=a $C_6$–$C_{10}$-aryl radical which is substituted by 1 to 4 fluorine, chlorine and/or bromine atoms, also represents a furyl or thienyl radical,
which comprises reducing an aluminum halide complex of the formula

 (II)

in which
$R^1$ and $R^2$ have the above mentioned meaning, and
Y represents fluorine, chlorine or bromine,
with an amineborane of the formula

 (III)

in which
$R^3$ represents $C_1$–$C_4$-alkyl and
$R^4$ represents hydrogen or $C_1$–$C_4$-alkyl and/or
with sodium borohydride and/or with potassium borohydride.

2. The process of claim 1, wherein the aluminum halide complex of the formula (II) is produced
by the Friedel-Crafts acylation of an aromatic or heteroaromatic compound of the formula

 (IV)

in which
$R^1$ has the meaning stated in claim 1,
with an acyl compound of the formula

 (V)

in which
$R^2$ has the meaning stated in claim 1, and
X represents fluorine, chlorine or bromine.

3. The process of claim 1, in which the aluminum halide complex of the formula (II) is produced
by the Friedel-Crafts acylation of a compound of the formula

 (VI)

in which
$R^2$ has the meaning stated in claim 1,
with an acyl compound of the formula

 (VII)

in which
$R^1$ has the meaning stated in claim 1, and
X represents fluorine, chlorine or bromine.

4. A process according to claim 1, wherein the aluminum halide complex is produced by the Friedel-Crafts acylation of an aromatic compound of the formula

 (IV)

with an acyl compound of the formula

 (V)

wherein
$R^2$ represents a phenyl radical which is unsubstituted or contains 1 to 3 substituents from the group consisting of fluorine and chlorine, or, if $R^1$ represents a $C_6$–$C_{10}$-aryl radical which is substituted by 1 to 4 fluorine, chlorine, and/or bromine atoms, also represents a furyl or thienyl radical, X represents chlorine or bromine, and independently and the aluminum halide complex thus formed wherein Y is chlorine or bromine is reduced with an aminoborane of the formula

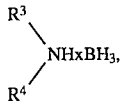  (III)

in which

R$^3$ represents methyl, ethyl or tert-butyl and
R$^4$ represents hydrogen, methyl or ethyl.

5. The process according to claim 1, wherein the aluminum halide complex is produced by the Freidel-Crafts acylation of a compound of the formula

R$^2$—H   (VI)

with an acyl compound of the formula

R$^1$—COX   (VII)

wherein

R$^2$ represents a phenyl radical which is unsubstituted or contains 1 to 3 substituents from the group consisting of fluorine and chlorine, or, if R$^1$ represents a C$_6$–C$_{10}$-aryl radical which is substituted by 1 to 4 fluorine, chlorine, and/or bromine atoms, also represents a furyl or thienyl radical, X represents chlorine or bromine, and independently,
is reduced with an aminoborane of the formula

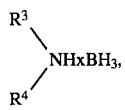  (III)

in which

R$^3$ represents methyl, ethyl or tert-butyl, and
R$^4$ represents hydrogen, methyl or ethyl.

6. The process according to claim 2 which comprises reacting an acyl compound of formula (V) with a compound of formula (IV) in the presence of an aluminum halide in an inert solvent; taking after the removal of the hydrogen halide, the resulting mixture which contains the aluminum halide complex of the formula II and reacting it with the aminoborane complex of formula III,

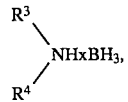  (III)

in which

R$^3$ represents C$_1$–C$_4$-alkyl and
R$^4$ represents hydrogen or C$_1$–C$_4$-alkyl sodium borohydride or potassium boro/hydride; hydrolyzing the resulting mixture with water to eliminate the aluminum halide; separating off the aqueous phase; and distilling the organic phase to obtain the resulting methylene compound.

7. The process according to claim 3 which comprises reacting an acyl compound of formula (VII) with a compound of formula (VI) in the presence of an aluminum halide; taking after the removal of the hydrogen halide, the resulting mixture which contains the aluminum halide complex of formula II and reacting with an aminoborane complex of the formula

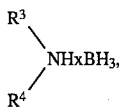  (III)

in which

R$^3$ represents C$_1$–C$_4$-alkyl and
R$^4$ represents hydrogen or C$_1$–C$_4$-alkyl sodium borohydride or potassium boro/hydride; hydrolizing the resulting mixture with water to eliminate the aluminum halide; separating off the aqueous phase; and distilling the organic phase to obtain the resulting methylene compound.

8. The process according to claim 2, wherein the acyl compound of formula (V) is reacted with a compound of formula (IV) at an initial temperature of −10° to +10° and, during the course of the reaction, raising the temperature to 50° C. to 110° C.

9. The process according to claim 3, wherein the acyl compound of formula (VII) is reacted with a compound of formula (VI) at an initial temperature of −10° to +10° and during the course of the reaction, raising the temperature to 50° C. to 110° C.

10. The process of claim 1, in which 0.5 to 1 mole of the boron-hydrogen compound is used per mole of aluminium halide complex of the formula (II).

11. 2-(2,4-Dichloro-5-fluorobenzyl)thiophene of the formula

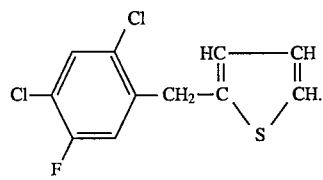  (I)

* * * * *

UNITED STATES PATENT AND TRADEMARK OFFICE
CERTIFICATE OF CORRECTION

PATENT NO. : 5,591,869
DATED : January 7, 1997
INVENTOR(S) : Fiege, et al.

It is certified that error appears in the above-indentified patent and that said Letters Patent is hereby corrected as shown below:

Col. 9, line 34   Delete " aminoborane " and substitute -- amineborane --

Col. 9, line 49   Delete " aminoborane " and substitute -- amineborane --

Col. 10, line 15  Delete " aminoborane " and substitute -- amineborane --

Signed and Sealed this

Seventeenth Day of June, 1997

Attest:

BRUCE LEHMAN

Attesting Officer

Commissioner of Patents and Trademarks